(12) United States Patent
Anand et al.

(10) Patent No.: US 12,220,569 B2
(45) Date of Patent: Feb. 11, 2025

(54) MEDICAL DEVICE FOR TREATING DECOMPENSATED HEART FAILURE

(71) Applicant: BOSTON SCIENTIFIC SCIMED, INC., Maple Grove, MN (US)

(72) Inventors: Umang Anand, Plymouth, MN (US); Ian Meredith, Boston, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 114 days.

(21) Appl. No.: 17/199,289

(22) Filed: Mar. 11, 2021

(65) Prior Publication Data
US 2021/0299431 A1    Sep. 30, 2021

Related U.S. Application Data

(60) Provisional application No. 62/994,572, filed on Mar. 25, 2020.

(51) Int. Cl.
*A61M 60/135*    (2021.01)
*A61M 60/295*    (2021.01)
(Continued)

(52) U.S. Cl.
CPC ........ *A61M 60/135* (2021.01); *A61M 60/295* (2021.01); *A61M 60/531* (2021.01);
(Continued)

(58) Field of Classification Search
CPC .............. A61M 60/135; A61M 60/531; A61M 60/295; A61M 2025/0003; A61M 2025/3306
See application file for complete search history.

(56) References Cited

U.S. PATENT DOCUMENTS

| 4,546,759 A | 10/1985 | Solar |
| 4,798,588 A | 1/1989 | Aillon |

(Continued)

FOREIGN PATENT DOCUMENTS

| EP | 2335768 A2 | 6/2011 |
| EP | 2335768 A4 | 1/2012 |

(Continued)

OTHER PUBLICATIONS

Agarwal et al; "Temporal Trends in Hospitalization for Acute Decompensated Heart Failure in the United States, 1998-2011," American Journal of Epidemiology, vol. 183, Issue 5, pp. 462-470, Mar. 2016. Accessed Jul. 18, 2022.

(Continued)

*Primary Examiner* — Rex R Holmes
*Assistant Examiner* — Jennifer L Ghand
(74) *Attorney, Agent, or Firm* — Seager, Tufte & Wickhem, LLP

(57) ABSTRACT

Medical device systems and methods for making and using medical device systems are disclosed. An example medical device system includes a control system having a processor and a pump, a first expandable member coupled to the processor and configured to be positioned in the superior vena cava. The system also includes a second expandable member coupled to the processor and configured to be positioned in the inferior vena cava. The system also includes a first sensing member designed to sense a first parameter. The system also includes a second sensing member designed to sense a second parameter. Additionally, the pump is designed to expand or contract the first expandable member, the second expandable member or both the first and the second expandable members based on a change in the first parameter, the second parameter or a change in both the first and the second parameters.

18 Claims, 13 Drawing Sheets

(51) Int. Cl.
*A61M 60/531* (2021.01)
*A61M 25/00* (2006.01)
*A61M 60/427* (2021.01)

(52) U.S. Cl.
CPC ... *A61M 2025/0003* (2013.01); *A61M 60/427* (2021.01); *A61M 2205/3306* (2013.01)

(56) References Cited

U.S. PATENT DOCUMENTS

| | | | | |
|---|---|---|---|---|
| 5,433,700 | A | * | 7/1995 | Peters ............... A61M 25/0026 604/113 |
| 5,762,624 | A | | 6/1998 | Peters |
| 5,810,757 | A | | 9/1998 | Sweezer, Jr. et al. |
| 6,071,271 | A | * | 6/2000 | Baker ............... A61M 25/1011 604/523 |
| 6,241,699 | B1 | | 6/2001 | Suresh et al. |
| 6,508,777 | B1 | * | 1/2003 | Macoviak ............ A61M 1/3659 604/9 |
| 6,555,057 | B1 | * | 4/2003 | Barbut ............... A61M 1/3621 604/113 |
| 8,968,239 | B2 | | 3/2015 | Herrera |
| 2003/0191448 | A1 | * | 10/2003 | Swindle ............. A61M 25/1011 604/509 |
| 2006/0064059 | A1 | | 3/2006 | Gelfand et al. |
| 2006/0074399 | A1 | | 4/2006 | Bates |
| 2008/0082132 | A1 | * | 4/2008 | Annest ................ A61N 1/3987 607/4 |
| 2010/0042175 | A1 | * | 2/2010 | Liu .................... A61N 1/36564 607/23 |
| 2010/0026497 | A1 | | 4/2010 | Choi et al. |
| 2010/0185220 | A1 | * | 7/2010 | Naghavi ............ A61B 5/14546 600/301 |
| 2010/0318114 | A1 | | 12/2010 | Pranevicius et al. |
| 2011/0112308 | A1 | | 5/2011 | Acemoglu et al. |
| 2011/0224606 | A1 | * | 9/2011 | Shome ............. A61M 25/10184 604/96.01 |
| 2011/0295301 | A1 | | 12/2011 | Hoem et al. |
| 2016/0263356 | A1 | * | 9/2016 | Selim .................. A61M 1/3666 |
| 2017/0049946 | A1 | * | 2/2017 | Kapur ................ A61M 60/295 |
| 2018/0169313 | A1 | | 6/2018 | Schwammenthal et al. |
| 2018/0169414 | A1 | * | 6/2018 | Goedeke ............. A61B 5/7246 |
| 2019/0126014 | A1 | | 5/2019 | Kapur et al. |
| 2020/0038566 | A1 | * | 2/2020 | Johnson .......... A61B 17/12036 |
| 2021/0177425 | A1 | * | 6/2021 | Kapur ................ A61M 60/161 |
| 2021/0187271 | A1 | * | 6/2021 | Mele .................. A61M 60/157 |

FOREIGN PATENT DOCUMENTS

| | | |
|---|---|---|
| JP | 2017209501 A | 11/2017 |
| RU | 2011112308 A | 10/2012 |
| WO | 9951286 A1 | 10/1999 |
| WO | 2010026497 A2 | 3/2010 |
| WO | 2010026497 A3 | 9/2010 |
| WO | 2018132623 A1 | 7/2018 |
| WO | 2018217846 A1 | 11/2018 |

OTHER PUBLICATIONS

Cooper et al; "Hemodynamic Predictors of Heart Failure Morbidity and Mortality: Fluid or Flow?," J Card Fail, vol. 22, No. 3, pp. 182-189, Mar. 2016.

Felkner et al.; American Heart Journal, vol. 45, Issue 2, Supplement, pp. S18-S25, Feb. 2003. Accessed Jul. 18, 2022.

Herrera, "Caval Flow Regulator Catheter Balloon for Heart Failure Treatment," Cardiovascular Research Foundation, TCT 2016, 14 pages, 2016.

Kapur et al; "Ventricular and Pulmonary Decompression: Intravenous Balloon Occlusion the PreCardia Device Concept," Tufts Medical Center, The Cardiovascular Center, TCT 2018, 28 pages, 2018.

Ross et al; "Recent National Trends in Readmission Rates After Heart Failure Hospitalization," Circulation Heart Failure, vol. 3, No. 1, pp. 97-103, Jan. 2010.

International Search Report and Written Opinion dated Jun. 10, 2021 for International Application No. PCT/US2021/021998.

* cited by examiner

MEDICAL DEVICE FOR TREATING DECOMPENSATED HEART FAILURE

CROSS-REFERENCE TO RELATED APPLICATIONS

This application claims the benefit of priority under 35 U.S.C. § 119 to U.S. Provisional Application Ser. No. 62/994,572, filed Mar. 25, 2020, the entirety of which is incorporated herein by reference.

TECHNICAL FIELD

The present disclosure pertains to medical devices, and methods for manufacturing medical devices. More particularly, the present disclosure pertains to medical devices including expandable members and pressure sensors connected with other structures, and methods for manufacturing and using such devices.

BACKGROUND

A wide variety of intracorporeal medical devices have been developed for medical use, for example, intravascular use. Some of these devices include guidewires, balloon catheters, sensors and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device system for treating a heart includes a control system having a processor and a pump, a first expandable member coupled to the processor, wherein the first expandable member is configured to be positioned in the superior vena cava. The system also includes a second expandable member coupled to the processor, wherein the second expandable member is configured to be positioned in the inferior vena cava. The system also includes a first sensing member having a first end positioned adjacent the first expandable member and a second end coupled to the control system, the first sensing member designed to sense a first parameter. The system also includes a second sensing member having a first end positioned adjacent the second expandable member and a second end coupled to the control system, the second sensing member designed to sense a second parameter. Additionally, the pump is designed to expand or contract the first expandable member, the second expandable member or both the first and the second expandable members based on a change in the first parameter, the second parameter or a change in both the first and the second parameters.

Alternatively or additionally to any of the embodiments above, wherein the first parameter, the second parameter or both the first parameter and the second parameter is blood pressure.

Alternatively or additionally to any of the embodiments above, wherein the first sensing member, the second sensing member or both the first sensing member and the second sensing member includes a MEMS sensor.

Alternatively or additionally to any of the embodiments above, wherein the first sensing member, the second sensing member or both the first sensing member and the second sensing member includes a fiber optic sensor.

Alternatively or additionally to any of the embodiments above, wherein the first sensing member, the second sensing member or both the first sensing member and the second sensing member includes a fluid-filled pressure sensing catheter.

Alternatively or additionally to any of the embodiments above, wherein the first expandable member is configured to be positioned in the superior vena cava after the first expandable member has been tracked through the jugular vein and wherein second expandable member is configured to be positioned in the inferior vena cava after the second expandable member has been tracked through the femoral vein.

Alternatively or additionally to any of the embodiments above, wherein the first expandable member is configured to be positioned in the superior vena cava and the second expandable member is configured to be positioned in the inferior vena cava after both the first expandable member and the second expandable member have been tracked through the femoral vein.

Alternatively or additionally to any of the embodiments above, further comprising a third sensing member having a first end positioned adjacent the first expandable member and a second end coupled to the control system, the third sensing member designed to sense a third parameter.

Alternatively or additionally to any of the embodiments above, further comprising a fourth sensing member having a first end positioned adjacent the second expandable member and a second end coupled to the control system, the fourth sensing member designed to sense a fourth parameter.

Alternatively or additionally to any of the embodiments above, wherein the first expandable member is positioned between a distal end of the first sensing member and a distal end of the third sensing member.

Alternatively or additionally to any of the embodiments above, further comprising a first elongate shaft having a first end coupled to the first expandable member, a second end coupled to the control system and a plurality of lumens extending therein, and wherein at least a portion of the first sensing member extends within at least a portion of a first lumen of the plurality of lumens.

Alternatively or additionally to any of the embodiments above, wherein at least a portion of the second sensing member extends within at least a portion of a second lumen of the plurality of lumens.

Alternatively or additionally to any of the embodiments above, further comprising a memory, the memory including a set of instructions executable by the processor, wherein the set of instructions is configured to expand both the first and the second expandable members based on a change in the first parameter, the second parameter or a change in both the first and the second parameters.

Another medical device system for treating a heart includes a control system having a processor and a pump and a first expandable member coupled to the processor, wherein the first expandable member is configured to be positioned in the superior vena cava. The system also includes a second expandable member coupled to the processor, wherein the second expandable member is configured to be positioned in the inferior vena cava. The system also includes a first pressure sensing member having a first end positioned adjacent the first expandable member and a second end coupled to the control system, the first pressure sensing member designed to sense a first parameter. The system also includes a second pressure sensing member having a first end positioned adjacent the second expandable member and a second end coupled to the control system, the second pressure sensing member designed to sense a second parameter. The system also includes a third pressure sensing member having a first end positioned adjacent the first expandable member and a second end coupled to the control system, the third pressure sensing member designed to sense a third parameter. The system also includes a fourth pressure sensing member having a first end positioned adjacent the second expandable member and a second end coupled to the control system, the fourth pressure sensing member designed to sense a fourth parameter. Additionally, the pump is designed to expand or contract the first expandable member, the second expandable member or both the first and the second expandable members based on a change in the first parameter, the second parameter, the third parameter or the fourth parameter.

Alternatively or additionally to any of the embodiments above, wherein the wherein the first parameter, the second parameter or both the first parameter and the second parameter is blood pressure.

Alternatively or additionally to any of the embodiments above, wherein the first sensing member, the second sensing member or both the first sensing member and the second sensing member includes a MEMS sensor.

Alternatively or additionally to any of the embodiments above, wherein the first sensing member, the second sensing member or both the first sensing member and the second sensing member includes a fiber optic sensor.

Alternatively or additionally to any of the embodiments above, wherein the first expandable member is positioned between a distal end of the first sensing member and a distal end of the third sensing member.

Alternatively or additionally to any of the embodiments above, further comprising a memory, the memory including a set of instructions executable by the processor, wherein the set of instructions is configured to expand both the first and the second expandable members based on a change in the first parameter, the second parameter or a change in both the first and the second parameters.

An example method for treating the heart includes advancing a first medical device into the superior vena cava through the jugular vein, the first medical device including a first expandable member and a first sensing member, both the first expandable member and the first sensing member coupled to a control system. The method also includes advancing a second medical device into the inferior vena cava through the femoral vein, the second medical device including a second expandable member and a second sensing member, both the second expandable member and the second sensing member coupled to the control system. The method also includes sensing a first parameter with the first sensing member, sensing a second parameter with the second sensing member and expanding the first expandable member, the second expandable member or both the first and the second expandable members based on a change in the first parameter, a change in the second parameter, or a change in both the first and the second parameters.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
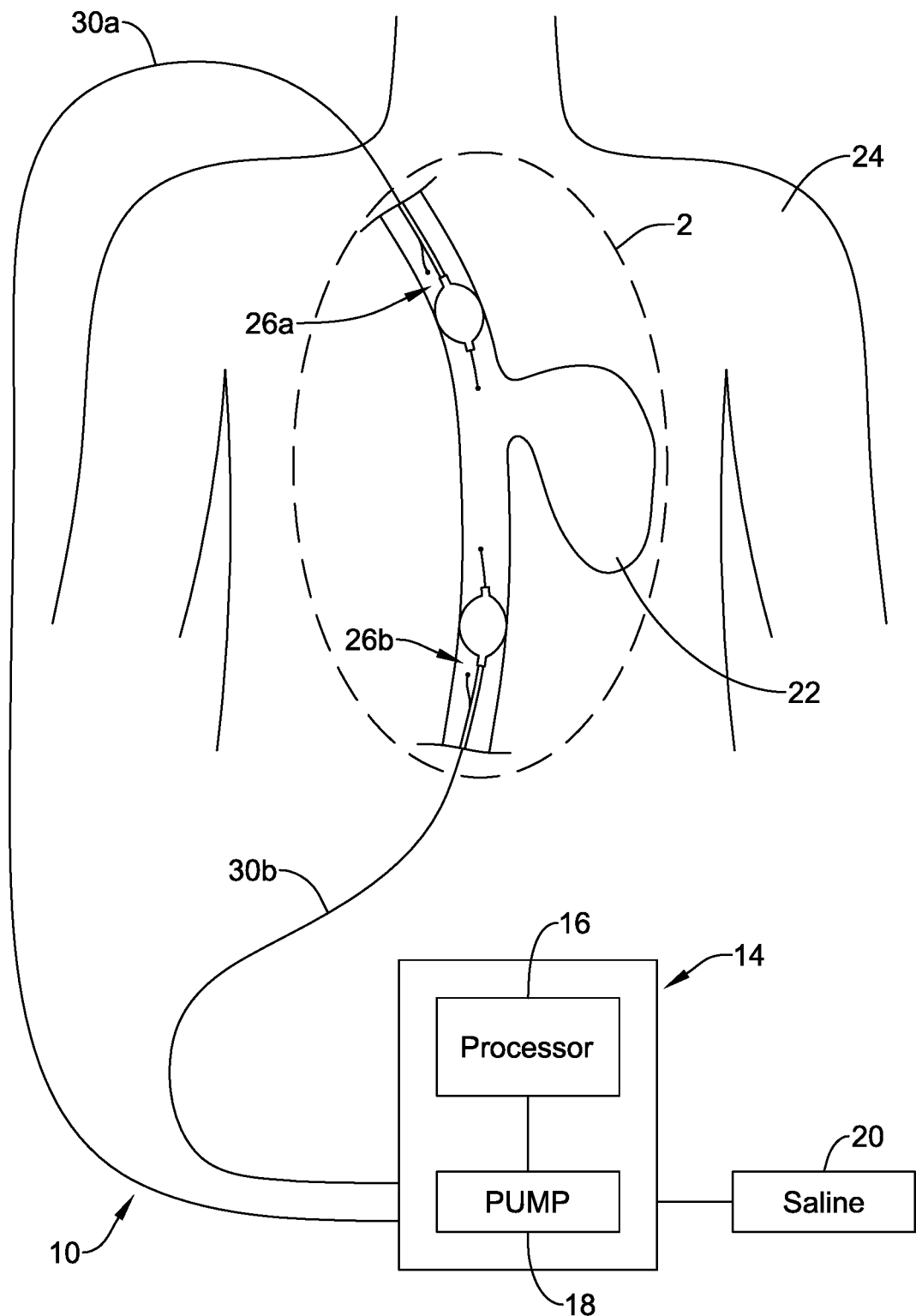
FIG. 1 illustrates an example medical device system.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

The heart is an essential organ in humans, responsible for pumping blood throughout the human body. Consequently, it is fundamentally important that the mechanical pumping properties of the heart operate correctly. When the heart does not operate correctly, a variety of adverse medical conditions may arise. These adverse medical conditions may include a severe condition called acute decompensated heart failure ("ADHF"). This form of heart failure may be characterized by the sudden inability of the heart to pump efficiently. However, this inability of the heart to pump efficiently is not due to cardiac arrest, as the heart does not stop even though the heart's pumping action significantly deteriorates.

ADHF results in an inability of a failing heart to pump blood in a forward direction. Further, the inability of the heart to pump blood in a forward direction may result in excess blood backing up (e.g., collecting) in one or more chambers of the heart. For example, if a patient's left ventricle is compromised and cannot effectively pump blood into the aorta, a progressive backup of blood may eventually manifest in the right atrium. The backup of blood in the right atrium may result in a variety of adverse complications. For example, the excess blood in the right atrium may cause increased blood pressure in the right atrium, eventually resulting in the shifting of the intraventricular septum, and thereby reducing left ventricle capacitance and stroke volume.

Therefore, in some instances, it may be desirable to position and expand an expandable medical device within the superior vena cava and/or the inferior vena cava to modulate the blood flow into the right atrium, thereby allowing the excess blood in the right atrium time to vacate and, consequently, lower the blood pressure in the right atrium. Example medical devices designed to be positioned within the superior vena cava and/or the inferior vena cava to modulate the blood flow into the right atrium are disclosed.

FIG. 1 illustrates an example medical device system 10. The medical device system 10 may include a first medical device 26a and a second medical device 26b. As will be described in greater detail below with respect to FIG. 2, each of the first medical device 26a and the second medical device 26b may include a distal end region positioned adjacent to the heart 22 of a patient 24. Additionally, the first medical device 26a may include an elongate member 30a extending out of and away from the patient 24, whereby the proximal end of the elongate member 30a may be coupled to a control system 14. Similarly, the second medical device 26b may include an elongate member 30b out of and away from the patient 24, whereby the proximal end of the elongate member 30a may be coupled to the control system 14.

The control system 14 described above may include a processor 16 and a pump 18. It can be appreciated that, in some examples, the processor 16 and the pump 18 may be located in a single console (e.g., housing). However, it can be further appreciated that, in other examples, the processor 16 and the pump 18 may be separate components spaced away from one another. In either arrangement, it can be appreciated that the processor 16 and the pump 18 may be able to communicate with one another. For example, the processor 16 may communicate with the pump 18 in response to physiological changes in the patient's body. It can be further appreciated that that processor 16 and the pump 18 may communicate through a variety of channels. For example, the processor 16 and the pump 18 may be hardwired with one another, or they may be wirelessly connected, or include both hardwired and wireless connections.

Additionally, in some examples the medical device system 10 may include a saline reservoir 20 (e.g., a saline bag) coupled to the control system 14. Specifically, in some examples, the saline reservoir 20 may be directly attached to the pump 18. The pump 18 may draw saline from the saline reservoir 20 in response to the processor 16 sensing physiological changes in a patient's body, as described above.

Figure 2:
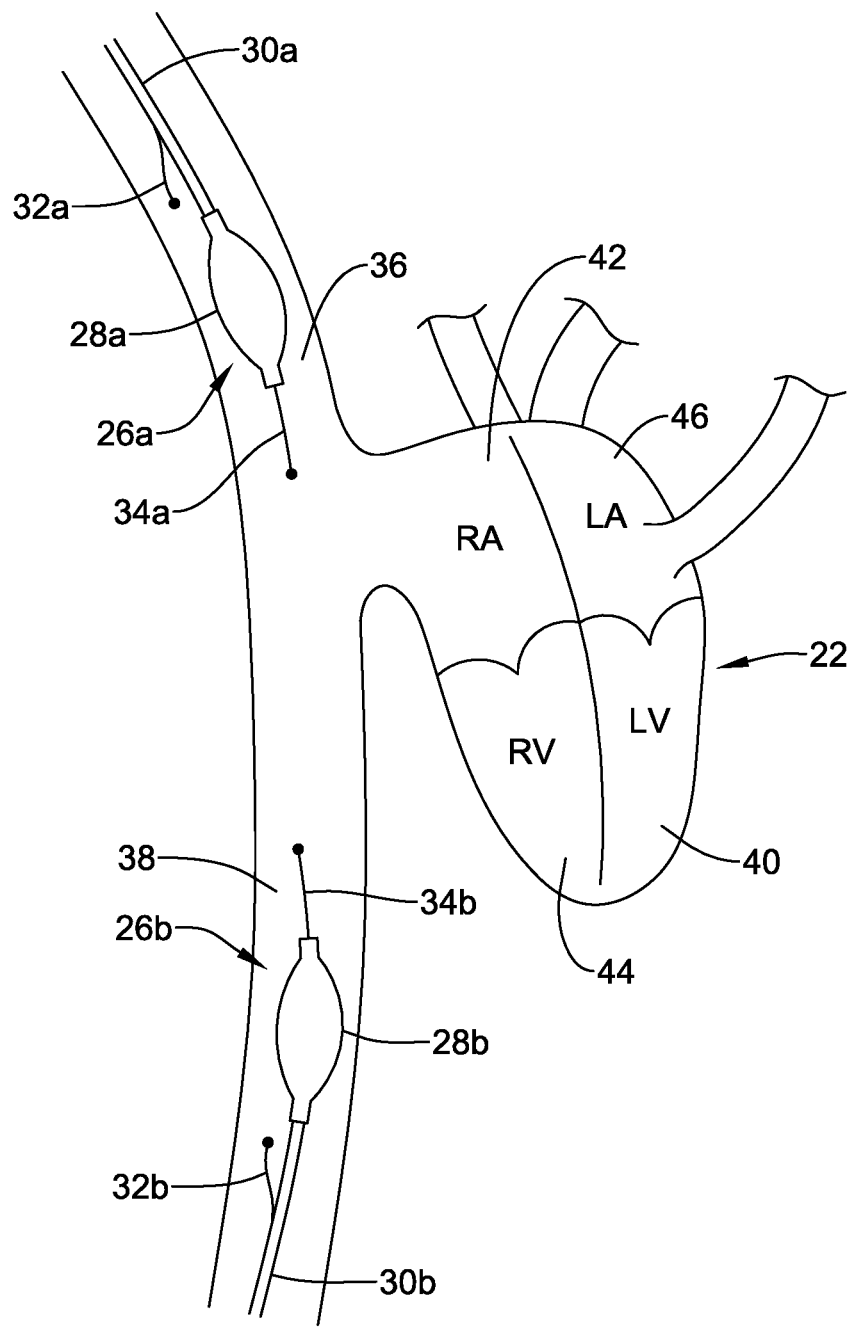
FIG. 2 is a schematic representation of an example medical device positioned in the superior vena cava and the inferior vena cava.

FIG. 2 illustrates the detailed view of FIG. 1. In particular, FIG. 2 illustrates the distal end region of the first medical device 26a positioned in the superior vena cava 36. As shown in FIG. 2, the first medical device 26a may include an expandable member 28a. In some instances, the expandable member 28a may be referred to as an expandable medical balloon. The expandable member 28a may include a distal end and a proximal end. The proximal end of the expandable member 28a may be coupled to the elongate member 30a (described above).

Further, it can be appreciated that the elongate member 30a may include one or more individual lumens extending therein. For example, it can be appreciated that the elongate member 30a may include an inflation lumen (not shown in FIG. 2, but visible in FIG. 5) which may be in fluid communication with the pump 18 (which, in turn, may be in fluid communication with the saline reservoir 20).

Additionally, FIG. 2 illustrates that the elongate member 30a may include one or more additional lumens (in addition to the inflation lumen described above) which are configured to permit a sensing member to extend therein. For example, FIG. 2 illustrates a sensing member 32a extending out of a portion of the elongate member 30a, whereby the distal end of the sensing member 32a may be positioned proximal of the expandable member 28a. Further, FIG. 2 illustrates a sensing member 34a extending out of the distal end region of the medical device 26a, whereby a portion of the sensing member 34a is positioned distally of the expandable member 28a.

Similarly to the above discussion regarding the first medical device 26a, FIG. 2 illustrates the distal end region of the second medical device 26b positioned in the inferior vena cava 38. As shown in FIG. 2, the second medical device 26b may include an expandable member 28b. In some instances, the expandable member 28b may be referred to as an expandable medical balloon. The expandable member 28b may include a distal end and a proximal end. The proximal end of the expandable member 28b may be coupled to the elongate member 30b (described above).

Further, it can be appreciated that the elongate member 30b may include one or more individual lumens extending therein. For example, it can be appreciated that the elongate member 30b may include an inflation lumen (not shown in FIG. 2, but visible in FIG. 5) which is in fluid communication with the pump 18 (which, in turn, is in fluid communication with the saline reservoir 20).

Additionally, FIG. 2 illustrates that the elongate member 30b may include one or more additional lumens (in addition to the inflation lumen described above) which are configured to permit a sensing member to extend therein. For example, FIG. 2 illustrates a sensing member 32b extending out of a portion of the elongate member 30b, whereby the distal end of the sensing member 32b may be positioned proximal of the expandable member 28b. Further, FIG. 2 illustrates a sensing member 34b extending out of the distal end region of the second medical device 26b, whereby a portion of the second sensing member 34b is positioned distally of the first expandable member 28b.

As described above, FIG. 2 illustrates the sensing members 32a/34a positioned adjacent the expandable member 28a in the superior vena cava 36. FIG. 2 further illustrates the sensing members 32b/34b positioned adjacent the expandable member 28b in the inferior vena cava 38. In some examples, the sensing members 32a/34a/32b/34b may all be configured to sense a change in one or more physiological parameters/characteristics occurring in a patient 24. Specifically, in some examples, the sensing members 32a/34a/32b/34b may include pressure sensing capabilities. In other words, the sensing member 32a may include a pressure sensor designed to measure the central venous pressure in the superior vena cava 36, the sensing members 34a/34b may include a pressure sensor designed to measure the right atrial pressure in a region adjacent to the right atrium 42 and the sensing member 32b may include a pressure sensor designed to measure the inferior venous pressure in the inferior vena cava 38.

It can be appreciated that the sensing members 32a/34a/32b/34b may include a variety of different configurations. For example, in some instances, each of the sensing members may include a microelectricalmechanical (MEMS) sensor coupled to an elongated wire. The MEMS pressure sensor may be able to detect and respond rapidly to very small changes in blood pressure. Further, a MEMS pressure sensor may be able to transmit a signal to the processor 16 indicating there has been a change in blood pressure in the region in which the MEMS sensor is disposed (e.g., the superior vena cava, inferior vena cava, or the adjacent the right atrium).

In other examples, each of the sensing members 32a/34a/32b/34b may include a pressure sensing catheter, whereby the catheter includes a fluid-filled lumen, the distal end of which may be open the surrounding environment. Further, a change in pressure in the area surrounding the distal end of the fluid-filled catheter may cause the fluid within the catheter to shift. This shifting of the fluid within the fluid-filled catheter may be sensed by the processor 16.

Additionally, in yet other examples, each of the sensing members 32a/34a/32b/34b may include a fiber optic pressure sensing catheter, whereby the fiber optic pressure sensing catheter includes a fiber optic pressure sensor. The fiber optic pressure sensor may sense a change in blood pressure (in areas adjacent to the sensor) based on a change in the light intensity surrounding the sensor. This change in light intensity may be sensed by the processor 16. In any of the examples discussed herein, the sensing members may include a variety of sensors. For example, in addition to the sensors discussed above, the sensing members disclosed herein may include piezo-resistive sensors, piezo-capacitive sensors, pressure sensors, flow sensors, accelerometers, temperature sensors, or the like.

As discussed above, when the pumping action of the heart 22 is compromised due to a weakened left ventricle 40 (for example), blood may begin to back up therein. Further, blood backing up in the left ventricle 40 may result in blood backing up in the left atrium 46. Further yet, blood backing up in the left atrium 46 may result in blood backing up within the pulmonary veins, the lungs and the pulmonary arteries. Blood backing up in the pulmonary arteries may further result in blood backing up the right ventricle 44 which, over time, results in the backing up of blood (and increased blood pressure) in the right atrium 42 and areas immediately adjacent to the right atrium 42 (e.g., the superior vena cava 36, the inferior vena cava 38).

Further, it can be appreciated that as the blood backs up into the right atrium 42, additional blood may continue to flow into the right atrium 42 from the superior vena cava 36 and the inferior vena cava 38. Therefore, to mediate the adverse effects caused by the backing up of blood into the right atrium 42 (e.g., the increase in blood volume and blood pressure within the right atrium 42), it may be desirable to temporarily occlude (fully or partially) the superior vena cava 36 and/or inferior vena cava 38.

Therefore, in some examples, one or more of the sensing members 32a/34a/32b/34b may sense a change in a physiological parameter (e.g., an increase in blood pressure) in the areas surrounding the superior vena cava 36, the inferior vena cava 38 and/or the right atrium 42. Further, it can be appreciated that any sensor sensing a change in the parameter may transmit a signal to the processor 16. The processor 16 may include a memory and/or an algorithm which is designed to measure, interpret, process, analyze, compute, evaluate, etc. the signal received from the one or more sensing members 32a/34a/32b/34b. Further yet, the algorithm may process the signal received from the one or more sensing members 32a/34a/32b/34b and, if necessary, communicate with the pump 18 to fill or evacuate fluid from the first expandable member 28a and/or the second expandable member 28b. As discussed above, the pump 18 may draw fluid from the saline reservoir 20 to expand the first expandable member 28a and/or the second expandable member 28b.

It can be appreciated that when the sensing members 32a/34a/32b/34b sense a change in a physiological parameter (e.g., an increase in blood pressure) in the areas surrounding the superior vena cava 36, the inferior vena cava 38 and/or the right atrium 42, expanding the first expandable member 28a and/or the second expandable member 28b may restrict the flow of blood into the areas surrounding the right atrium 42. Restricting the flow of blood into the areas surrounding the right atrium 42 may allow excess blood which has built up in the right atrium 42 to vacate (or partially vacate) the right atrium 42, thereby reducing the blood pressure built up in the heart 22.

In some instances, it may not be necessary for the system 10 to expand the first expandable member 28a and/or the second expandable member 28b to a point in which the expandable members 28a/28b completely occlude the superior vena cava 36 and the inferior vena cava 38, respectively. Rather, in some instances the processor 16 may process the signals received from one or more of the sensing members 32a/34a/32b/34b and only partially occlude the superior vena cava 36 and/or the inferior vena cava 38. In other instances, the processor 16 may process the signals received from one or more of the sensing members 32a/34a/32b/34b and fully occlude the superior vena cava 36 or the inferior vena cava 38 while leaving the other of the superior vena cava 36 and the inferior vena cava 38 open or only partially occluded. It can be appreciated that the processor 16 may include an algorithm which is designed to analyze varying physiological parameters occurring in the superior vena cava 36, the inferior vena cava 38 and/or the right atrium 42 to determine the degree to which either the first expandable member 28a and/or the second expandable member 28b should be occluded (if at all).

It is noted that the physiological parameters discussed above which may be processed by the processor 16 to assess the degree to which the first expandable member 28a and/or the second expandable member 28b should be occluded is not limited to merely the blood pressure in the superior vena cava 36, the inferior vena cava 38 and/or the right atrium 42. Rather, the processor 16 may assess blood flow, blood pressure, blood volume, motion of the inferior vena cava, motion of the superior vena cava, respiration cycles, volume in the inferior vena cava, volume in the superior vena cava or the like.

Further, in some instances the algorithm utilized by the processor 16 may include an assessment of the blood pressure readings in the superior vena cava 36, the inferior vena cava 38 and/or the right atrium 42 for a particular patient, whereby the algorithm may further utilize a look-up table or artificial intelligence algorithm to determine the degree to which either the first expandable member 28a and/or the second expandable member 28b should be occluded for that particular patient at a given time point.

Further yet, in some examples the control system 14 may also be coupled to a sensor which is providing a patient's ECG to the processor 16. In that case, the cardiac cycle timing of a particular patient may be utilized to determine the degree to which either the first expandable member 28a and/or the second expandable member 28b should be occluded for that particular patient at a given time point. Additionally, in some examples the control system 14 may also be coupled to a chest accelerometer (e.g., a wearable patch) which may sense the inspiration cycles for a given patient. The timing of the inspiration cycles of a particular patient may be utilized to determine the degree to which either the first expandable member 28a and/or the second expandable member 28b should be occluded for that particular patient at a given time point.

As discussed above, the timing of the inflation or evacuation of the first expandable member 28a may be different that the timing of inflation or evacuation of the second expandable member 28b. In other words, the inflation or evacuation of the first expandable member 28a may not be in sync with the inflation or evacuation of the second expandable member 28b. Permitting the inflation or evacuation of the first expandable member 28a to be out of sync with the second expandable member 28b may allow a minimal impact on cerebral blood flow without raising renal or hepatic venous pressures and reducing cardiac workload while maintaining overall mean arterial pressures.

Figure 3:
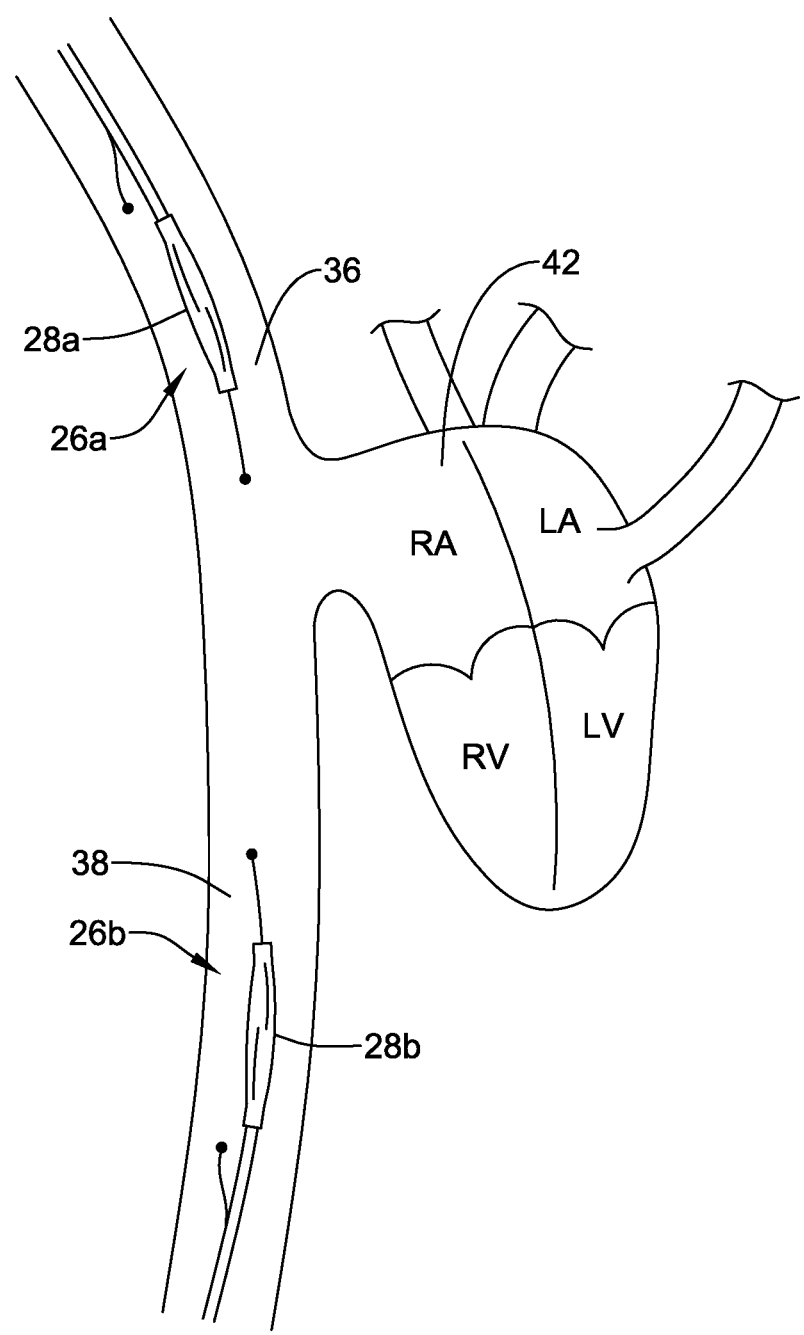
FIG. 3 is a schematic representation of an example medical device positioned in the superior vena cava and the inferior vena cava.

FIG. 3 illustrates the first medical device 26a positioned in the superior vena cava 36 as described above. Further, FIG. 3 illustrates the first expandable member 28a in a collapsed configuration (e.g., a configuration which may not be limiting blood flow through the superior vena cava 36 to the right atrium 42). Likewise, FIG. 3 illustrates the second medical device 26b positioned in the inferior vena cava 38 as described above. Further, FIG. 3 illustrates the second expandable member 26b in a collapsed configuration (e.g., a configuration which may not be limiting blood flow through the inferior vena cava 38 to the right atrium).

Figure 4:
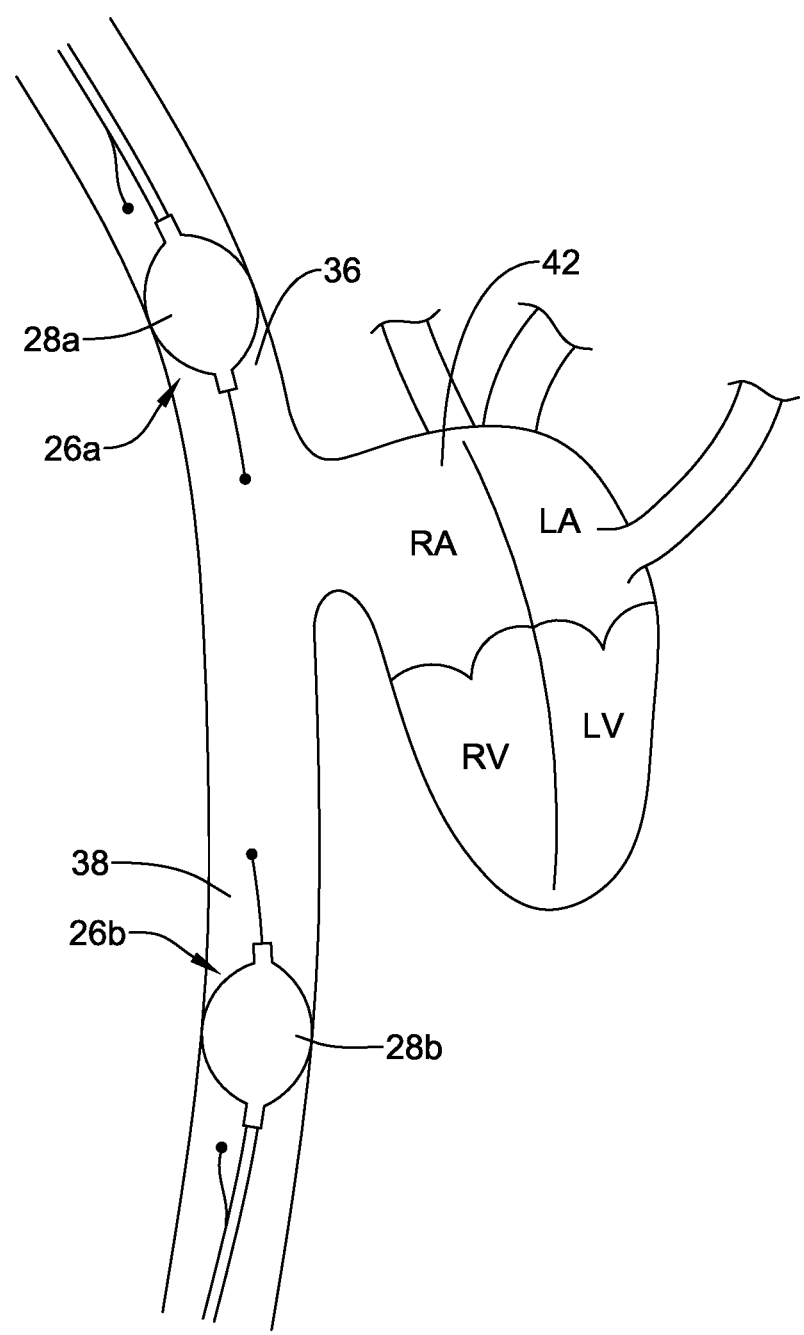
FIG. 4 is a schematic representation of an example medical device positioned in the superior vena cava and the inferior vena cava.

FIG. 4 illustrates the first medical device 26a positioned in the superior vena cava 36 as described above. Further, FIG. 4 illustrates the first expandable member 28a in an expanded configuration (e.g., a configuration which may be limiting blood flow through the superior vena cava 36 to the right atrium 42). Likewise, FIG. 4 illustrates the second medical device 26b positioned in the inferior vena cava 38 as described above. Further, FIG. 4 illustrates the second expandable member 26b in an expanded configuration (e.g., a configuration which may be limiting blood flow through the inferior vena cava 38 to the right atrium).

It can be appreciated from FIGS. 1-4 that, in some examples, the first medical device 26a may be inserted through an incision in a patient's neck and passed through the jugular vein to the superior vena cava 36. Further, it can be appreciated that, in some examples, the second medical device 26b may be inserted through an incision in a patient's groin and passed through the femoral vein to the inferior vena cava 38.

Figure 5:
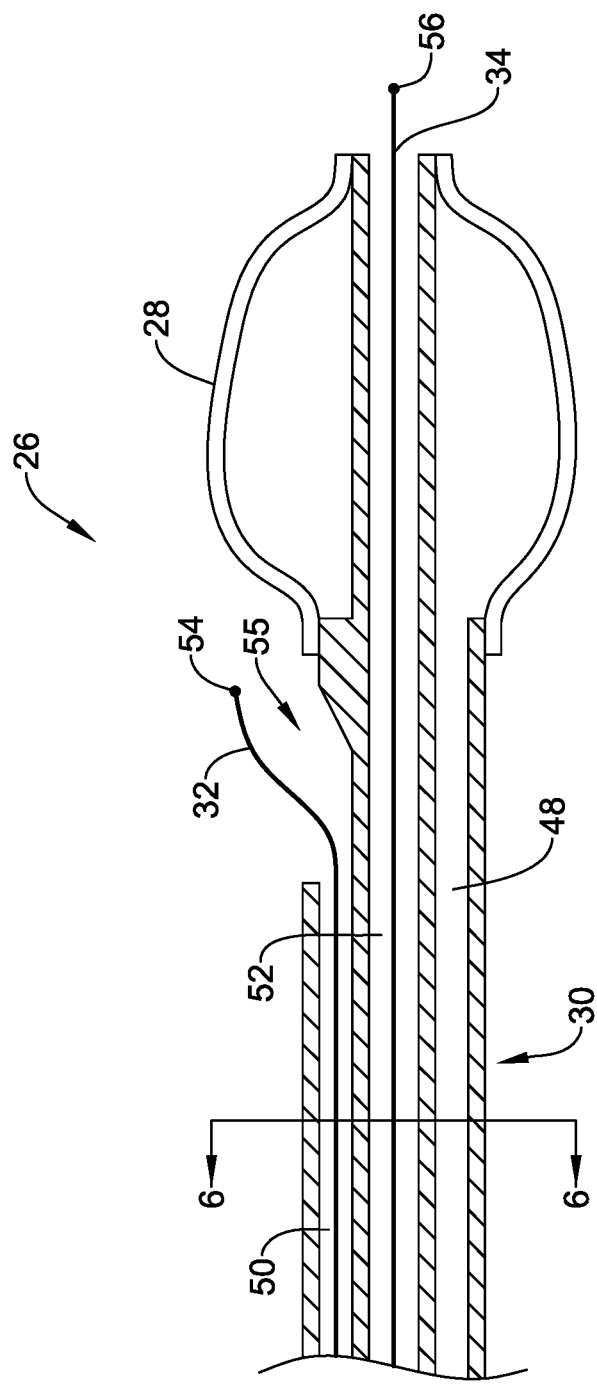
FIG. 5 illustrates a portion of an example medical device.

FIG. 5 illustrates an example medical device 26. For simplicity, the example medical device may illustrate the medical device 26a or the medical device 26b described above. FIG. 5 illustrates that the medical device 26 may include an expandable member 28. The expandable member 28 may be coupled to the distal end of an elongate member 30. A proximal end of the elongate shaft may be coupled to the control system 14 (including the processor 16 and the pump 18) as described above. Further, the elongate shaft 30 may include a first sensing member lumen 50 extending therein and a second sensing member lumen 52 extending therein. The first sensing member lumen 50 and the second sensing member lumen 52 may extend along the entire length of the elongate shaft 30 or along only a portion of the elongate member 30.

Additionally, FIG. 5 illustrates the sensing member 32 extending with the first sensing member lumen 50, whereby the sensing member 32 exits the elongate member 30 through an aperture 55. FIG. 5 also shows the sensing member 34 extending with the second sensing member lumen 52, whereby the sensing member 34 exits the elongate member 30 out of the distal end opening of the elongate member 30. Further, FIG. 5 illustrates an example sensor 54 disposed along the distal end of the sensing member 32 and another example sensor 56 disposed along the distal end of the sensing member 56. It can be appreciated that the sensing members 32/34 may include any of the types of sensing members described herein.

FIG. 5 further illustrates that the elongate member 30 may include an inflation lumen 48 extending within the elongate member 30. The inflation lumen 48 may be in fluid communication with the control system 14 (including the pump 18 and the saline reservoir 20). It can be appreciated that the distal end of the inflation lumen 48 opens into the expandable cavity of the expandable member 28.

Figure 6:
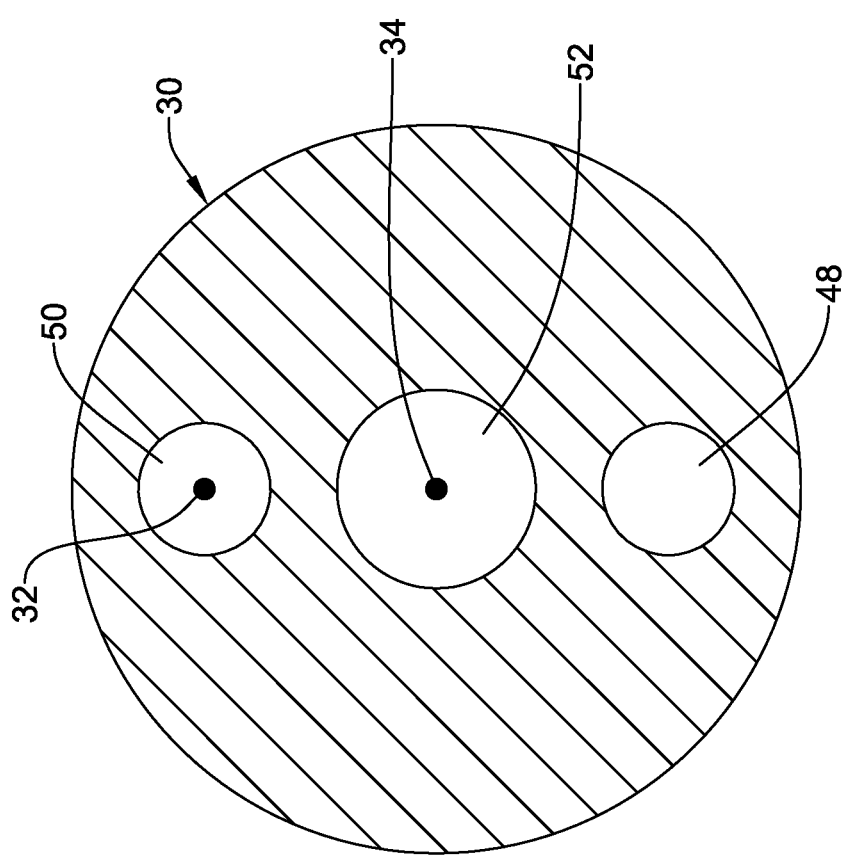
FIG. 6 is a cross-sectional illustration taken along line 6-6 of FIG. 5.

FIG. 6 is a cross-sectional illustration taken along line 6-6 of FIG. 5. FIG. 6 shows the first sensing member lumen 50, the second sensing member lumen 52 and the inflation lumen 48 extending within the elongate member 30. Further, FIG. 6 illustrates the first sensing member 32 extending within the first sensing member lumen 50 and the second sensing member 34 extending within the second sensing member lumen 52.

Figure 7:
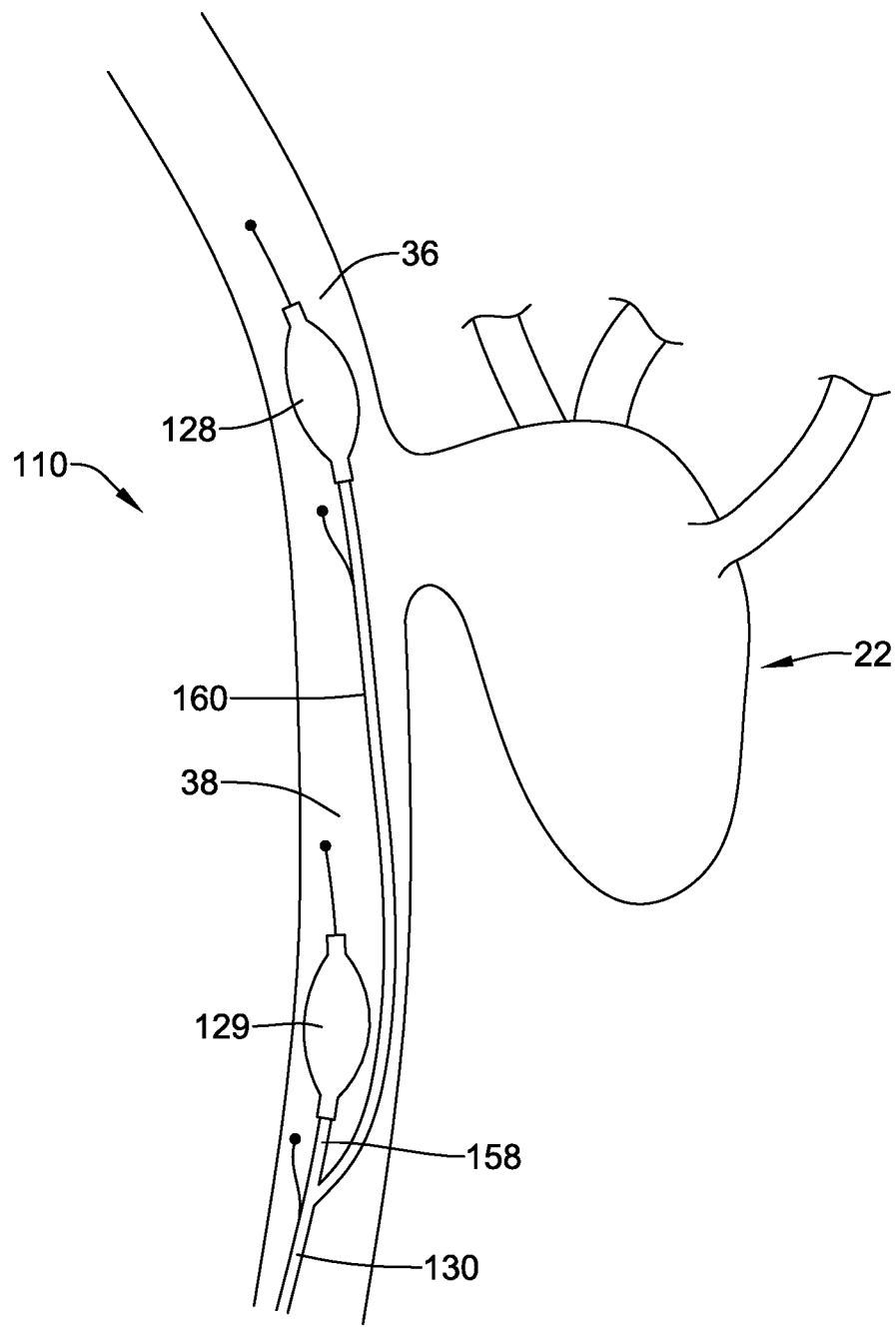
FIG. 7 is a schematic representation of an example medical device positioned in the superior vena cava and the inferior vena cava.

FIG. 7 illustrates another example medical device system 110 positioned adjacent the heart 22. The medical device 110 may be similar in form and function to the medical device system 10 described above. However, unlike the medical device system 10 described above, the medical device system 110 may include an elongate member 130 which branches into a proximal elongate shaft 158 and a distal elongate member 160. The proximal end of the elongate member 130 may be coupled to the control system 14 (include the pump 18 and processor 16) as described above.

Further, FIG. 7 illustrates that the distal elongate member 160 is coupled to a first expandable member 128 and the proximal elongate shaft is coupled to a second expandable member 129. The first expandable member 128 and/or the second expandable member 129 may be expanded to occlude the superior vena cava 36 and/or the inferior vena cava 38, as described above with respect to the medical device system 10.

Figure 8:
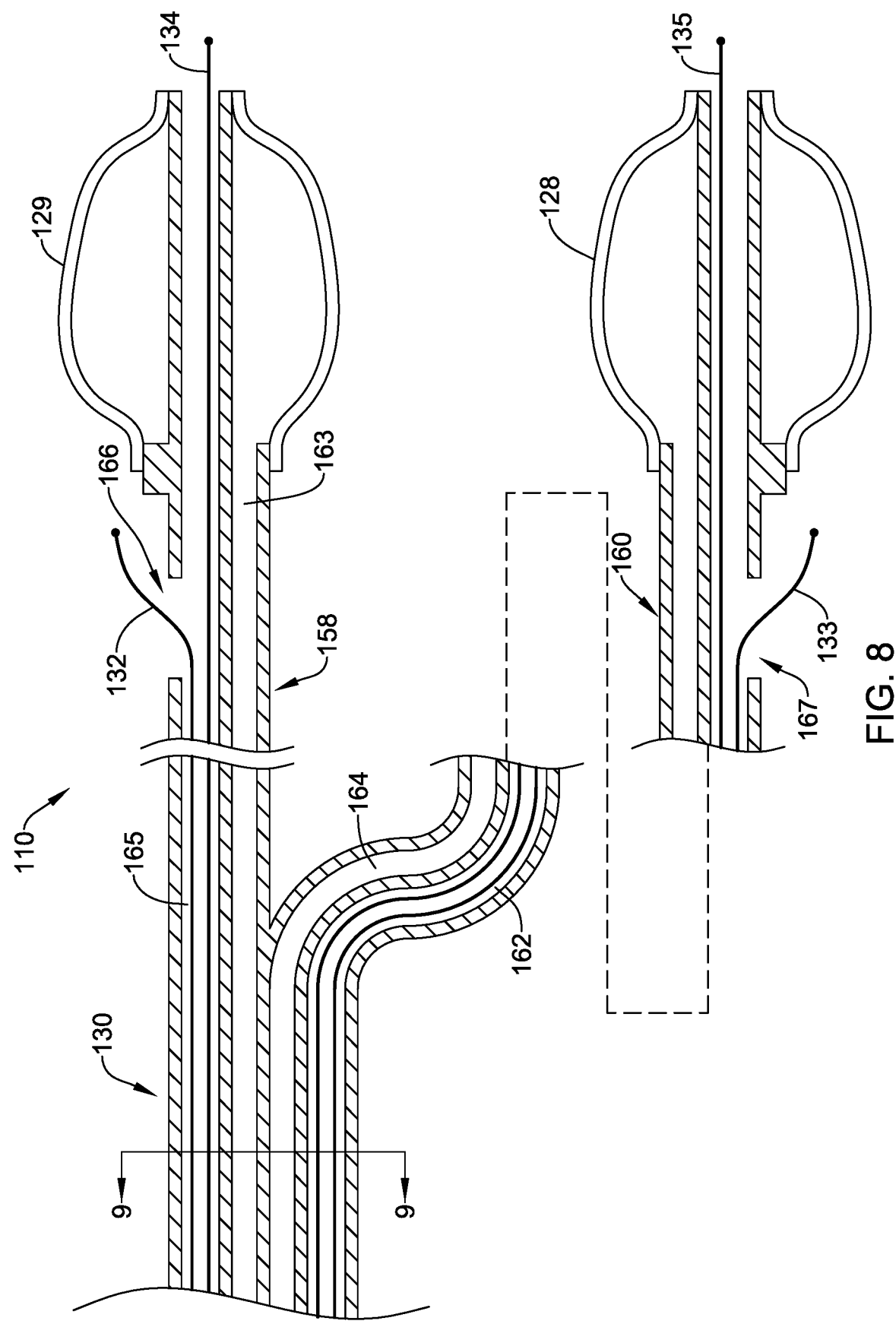
FIG. 8 illustrates a portion of another example medical device.

FIG. 8 illustrates that the medical device 110 may include an elongate member 130 which branches into a proximal elongate member 158 and a distal elongate member 160. FIG. 8 further illustrates the first expandable member 128 and the second expandable member 129. The first expandable member 128 may be coupled to the distal end of the distal elongate member 160 and the second expandable member 129 may be coupled to the distal end of the proximal elongate member 158. Additionally, a proximal end of the elongate member 130 may be coupled to the control system 14 (including the processor 16 and the pump 18) as described above.

Further, the elongate member 130 may include a first sensing member lumen 162 extending therein and a second sensing member lumen 165 extending therein. The first sensing member lumen 162 and the second sensing member lumen 165 may extend along the entire length of the elongate member 130 or along only a portion of the elongate member 130.

Additionally, FIG. 8 illustrates two sensing members 133/135 extending with the first sensing member lumen 162, whereby the sensing member 133 exits the distal elongate member 160 through an aperture 167. FIG. 8 also shows the sensing member 135 extending within the first sensing member lumen 162, whereby the sensing member 135 exits the distal elongate member 160 out of the distal end opening of the elongate member 160. Further, FIG. 8 illustrates two sensing members 132/134 extending within the second sensing member lumen 165, whereby the sensing member 132 exits the proximal elongate shaft 158 through an aperture 166. FIG. 8 also shows the sensing member 134 extending through the second sensing member lumen 165, whereby the sensing member 134 exits the proximal elongate member 158 out of the distal end opening of the proximal elongate shaft 158. It can be appreciated that the sensing members 132/133/134/135 may include any of the types of sensing members described herein.

FIG. 8 further illustrates that the distal elongate member 160 may include an inflation lumen 164 extending within the elongate member 160 and that the proximal elongate member 158 may include an inflation lumen 163 extending within the proximal elongate member 158. The inflation lumens 164/163 may be in fluid communication with the control system 14 (including the pump 18 and the saline reservoir 20). It can be appreciated that the distal end of the inflation lumen 164 opens into the expandable cavity of the expandable member 128 and the distal end of the inflation lumen 163 opens into the expandable cavity of the expandable member 129.

It can be appreciated from FIGS. 7-8 that the medical device 110 may be inserted through an incision in a patient's groin into the femoral vein where it may be further tracked to and deployed in the patient's superior vena cava 36 and inferior vena cava 38 as described above.

Figure 9:
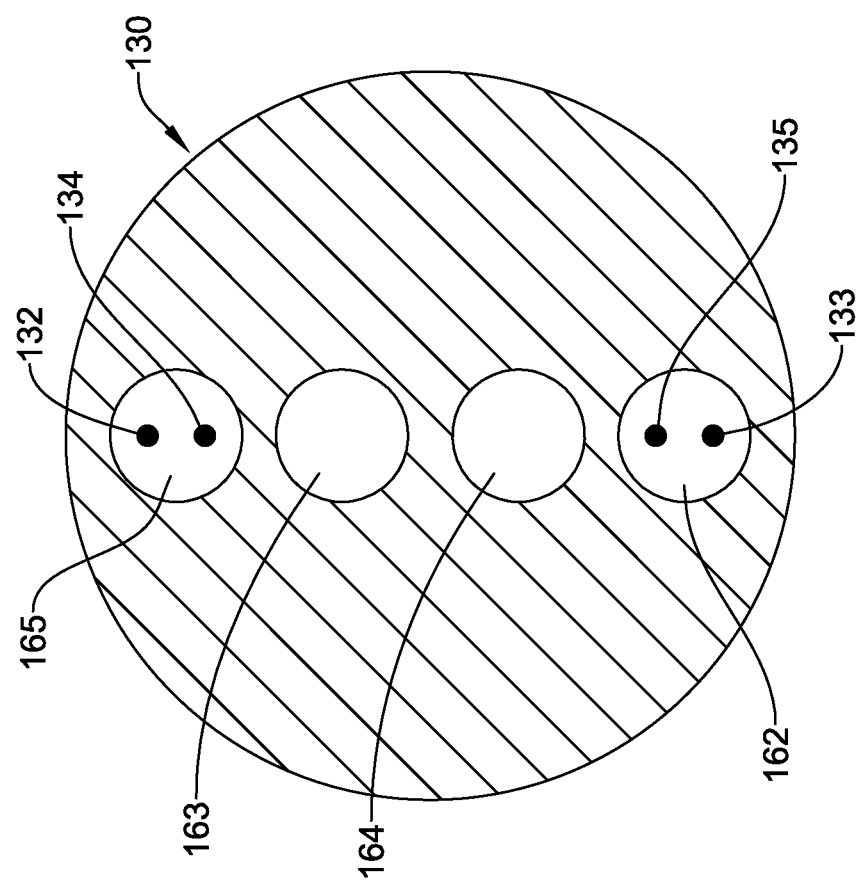
FIG. 9 is a cross-sectional illustration taken along line 9-9 of FIG. 8.

FIG. 9 is a cross-sectional illustration taken along line 9-9 of FIG. 8. FIG. 9 shows the first sensing member lumen 162, the second sensing member lumen 165, the inflation lumen 163 and the inflation lumen 164 extending within the elongate member 130. Further, FIG. 9 illustrates the sensing members 133/135 extending within the first sensing member lumen 162 and the second sensing members 132/134 extending within the second sensing member lumen 165.

Figure 10:
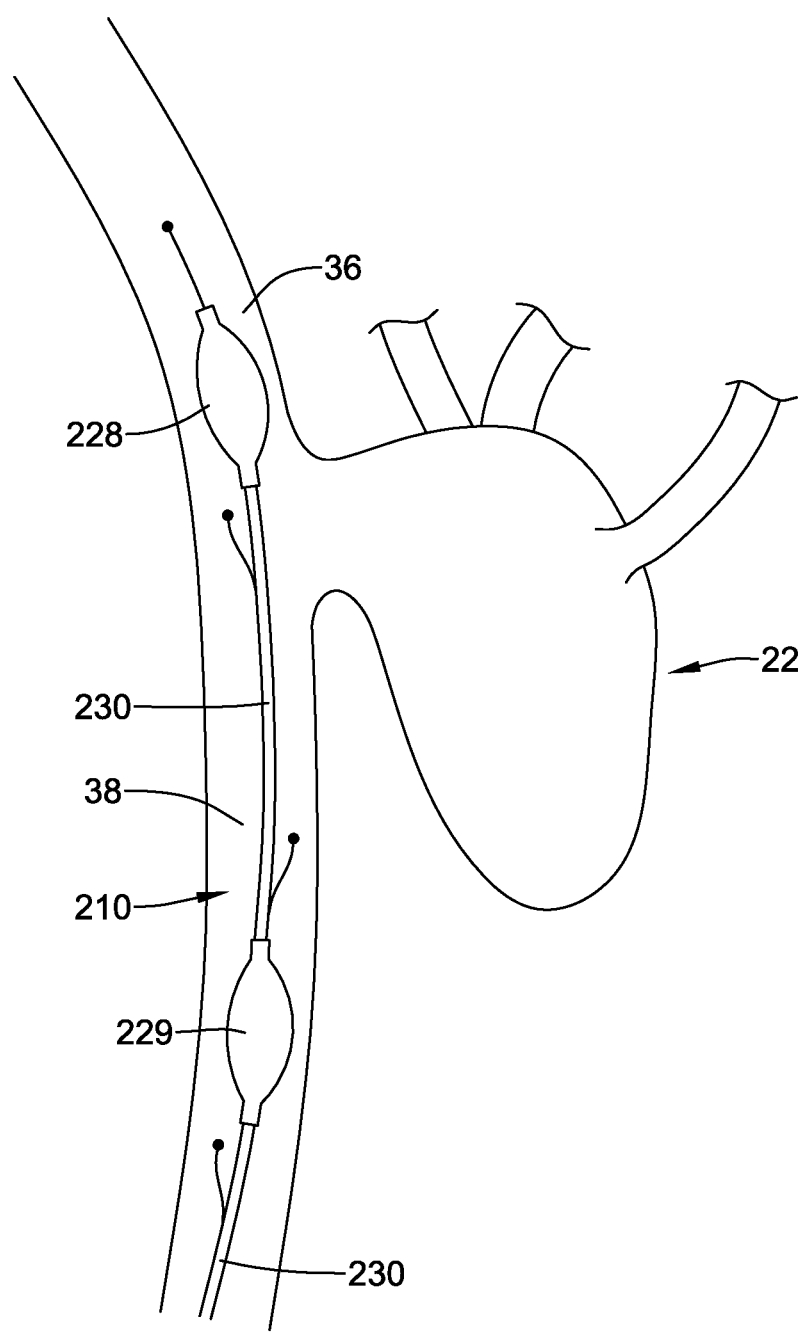
FIG. 10 is a schematic representation of an example medical device positioned in the superior vena cava and the inferior vena cava.

FIG. 10 illustrates another example medical device system 210 positioned adjacent the heart 22. The medical device 210 may be similar in form and function to the other medical device systems described above. However, unlike the medical device system systems described above, the medical device system 210 may include an elongate member 230 which passes through a second expandable member 229 and extends to a first expandable member 228. The proximal end of the elongate member 230 may be coupled to the control system 14 (include the pump 18 and processor 16) as described above.

Further, FIG. 10 illustrates that the first expandable member 228 and/or the second expandable member 229 may be expanded to occlude the superior vena cava 36 and/or the inferior vena cava 38, as described above with respect to the medical device system 10.

Figure 11:
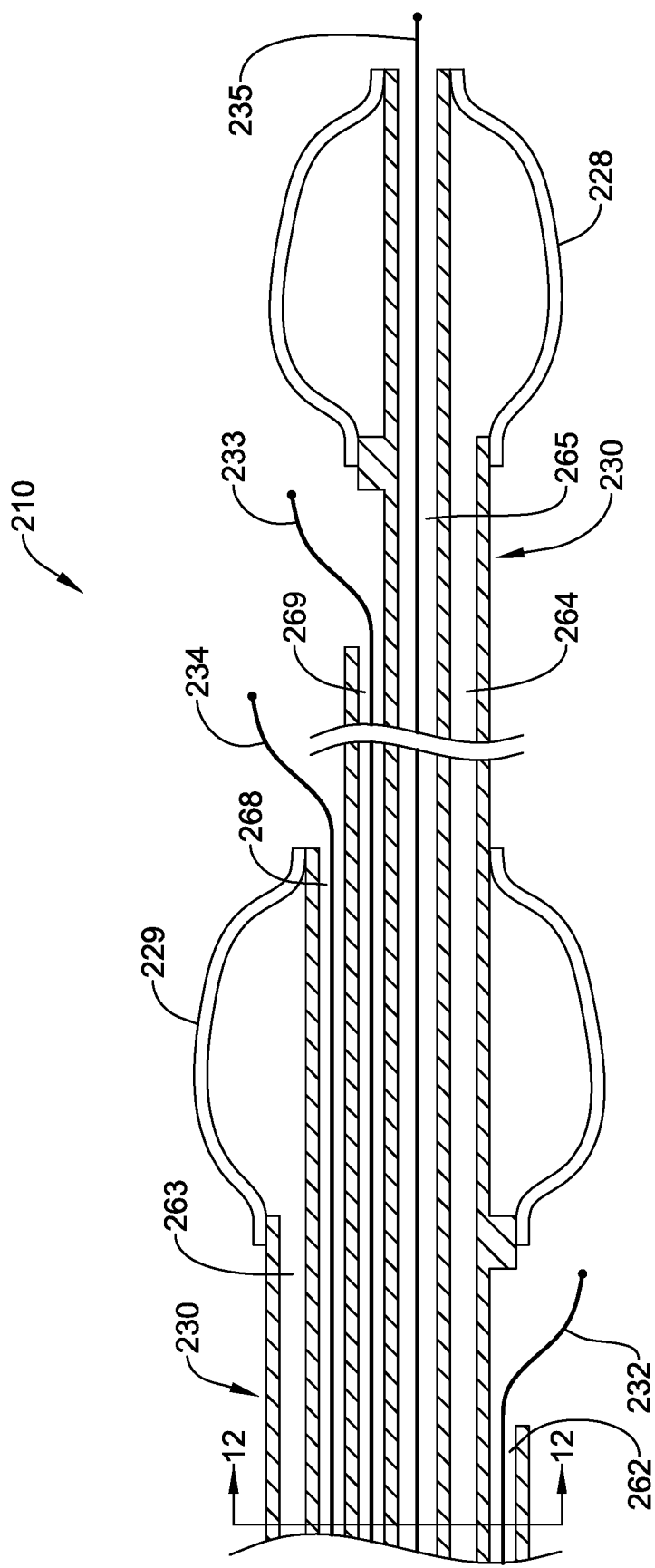
FIG. 11 illustrates a portion of another example medical device.

FIG. 11 illustrates the distal end region of the example medical device 210 described above. FIG. 11 illustrates that the medical device 210 may include an elongate member 230 which attaches to both a second expandable member 229 and a first expandable member 228 (e.g., a portion of the elongate member 230 passes through the second expandable member 229 and attaches to a first expandable member 228). FIG. 11 further illustrates that the medical device 210 may include the first expandable member 228 and the second expandable member 229. The first expandable member 228 may be coupled to the distal end of the elongate member 230 and the second expandable member 229 may be coupled to a mid-section of the elongate member 230. Additionally, a proximal end of the elongate member 230 may be coupled to the control system 14 (including the processor 16 and the pump 18) as described above.

Further, the elongate member 230 may include a first sensing member lumen 262, a second sensing member lumen 268, a third sensing member lumen 269 and a fourth sensing member lumen 265 extending therein. The first sensing member lumen 262, the second sensing member lumen 268, the third sensing member lumen 269 and/or the fourth sensing member lumen 265 may extend along the entire length of the elongate member 230 or along only a portion of the elongate member 230.

Additionally, FIG. 11 illustrates a sensing member 232 extending with the first sensing member lumen 262, a second sensing member 234 extending with the second sensing member lumen 268, a third sensing member 233 extending with the third sensing member lumen 269 and a fourth sensing member 235 extending with the fourth sensing member lumen 265.

FIG. 11 further illustrates that the elongate member 230 may include a first inflation lumen 264 and a second inflation lumen 263. The inflation lumens 263/264 may be in fluid communication with the control system 14 (including the pump 18 and the saline reservoir 20). It can be appreciated that the distal end of the first inflation lumen 264 may open into the expandable cavity of the first expandable member 228 and the distal end of the second inflation lumen 263 into the expandable cavity of the second expandable member 229.

It can be appreciated from FIGS. 10-11 that the medical device 210 may be inserted through an incision in a patient's groin into the femoral vein where it may then be further tracked to and deployed in the patient's superior vena cava and inferior vena cava 38 as described above.

Figure 12:
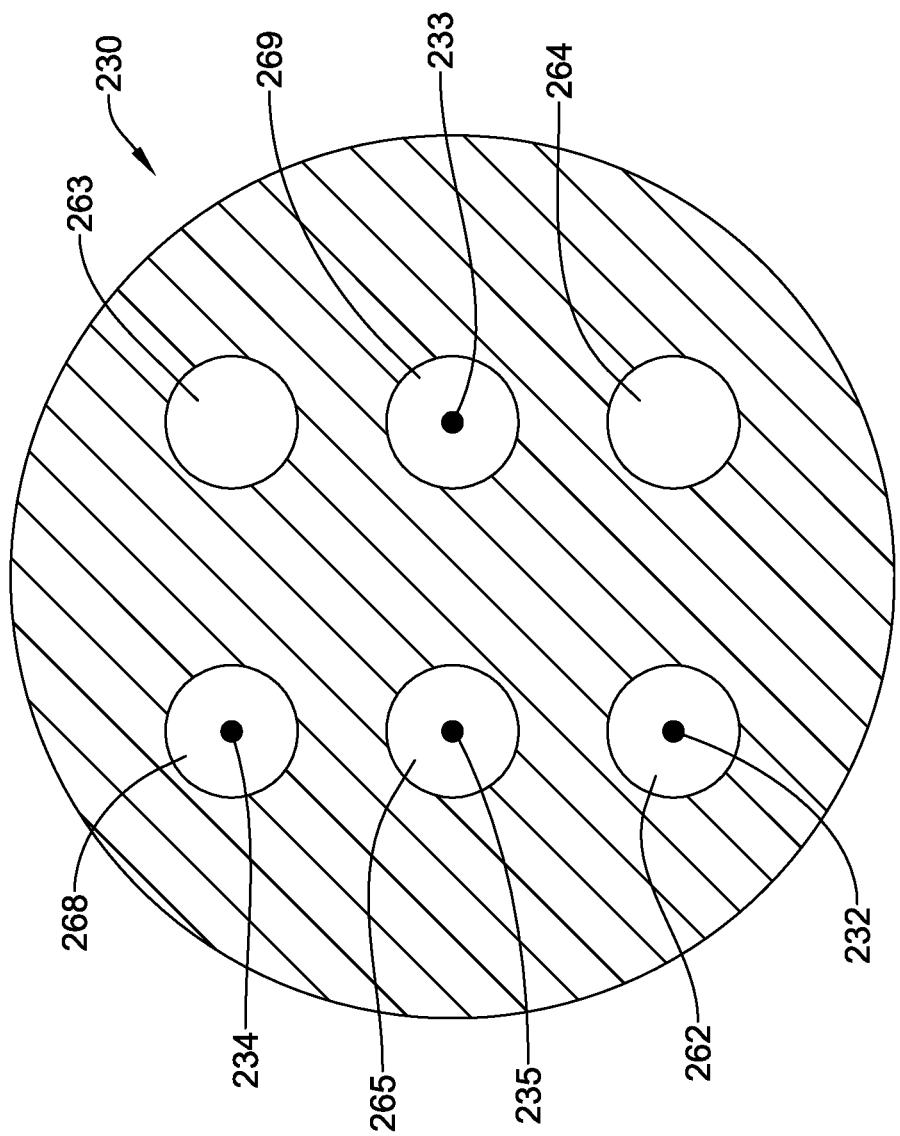
FIG. 12 is a cross-sectional illustration taken along line 12-12 of FIG. 11.

FIG. 12 is a cross-sectional illustration taken along line 12-12 of FIG. 11. FIG. 12 shows the first sensing member lumen 262, the second sensing member lumen 268, the third sensing member lumen 269, the fourth sensing member lumen 265, the inflation lumen 263 and the inflation lumen 264 extending within the elongate member 230. Further, FIG. 12 illustrates a sensing member 232 extending with the first sensing member lumen 262, a second sensing member 234 extending with the second sensing member lumen 268, a third sensing member 233 extending with the third sensing member lumen 269 and a fourth sensing member 235 extending with the fourth sensing member lumen 265.

Figure 13:
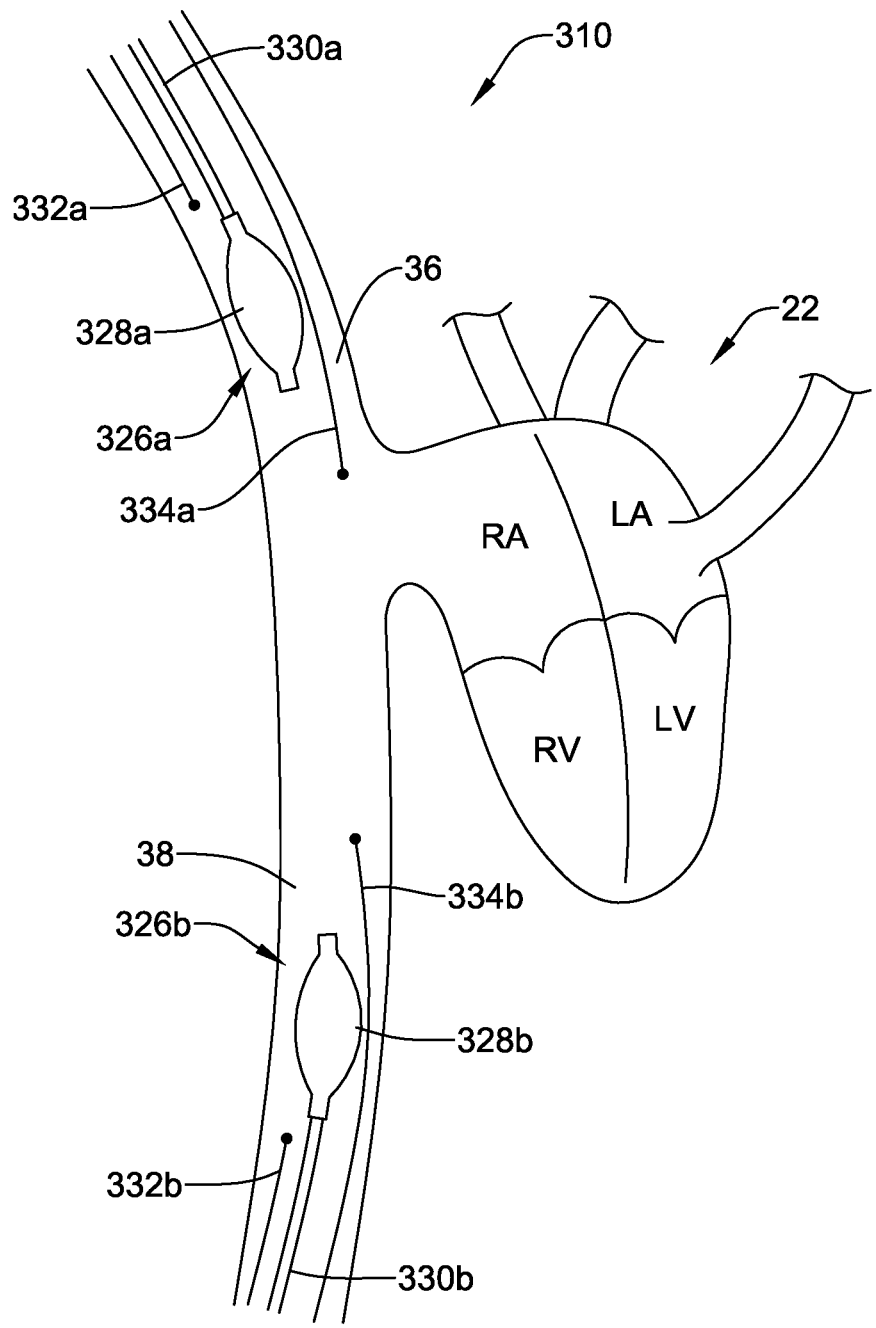
FIG. 13 is a schematic representation of an example medical device positioned in the superior vena cava and the inferior vena cava.

FIG. 13 illustrates another example medical device system 310. The medical device system 310 may include a first medical device 326a and a second medical device 326b. Each of the first medical device 326a and the second medical device 326b may include a distal end region positioned adjacent to the heart 22 of a patient 24 (not shown in FIG. 13, but shown in FIG. 1). Additionally, the first medical device 326a may include an elongate member 330a extending out of and away from the patient 24, whereby the proximal end of the elongate member 330a may be coupled to a control system 14 (not shown in FIG. 13, but shown in FIG. 1). Similarly, the second medical device 326b may include an elongate member 330b out of and away from the patient 24, whereby the proximal end of the elongate member 330a may be coupled to the control system 14.

FIG. 13 further illustrates the first medical device 326a may include an expandable member 328a. The distal end region of the first medical device 326a may be positioned in the superior vena cave 36. In some instances, the expandable member 328a may be referred to as an expandable medical balloon. The expandable member 328a may include a distal end and a proximal end. The proximal end of the expandable member 328a may be coupled to the elongate member 330a (described above). Further, it can be appreciated that the elongate member 330a may include one or more individual lumens extending therein. For example, it can be appreciated that the elongate member 330a may include an inflation lumen which may be in fluid communication with the pump 18 (which, in turn, may be in fluid communication with the saline reservoir 20). Both the pump 18 and the saline reservoir 20 are illustrated in FIG. 1.

Additionally, FIG. 13 illustrates that the distal end region of the second medical device 326b may be positioned in the inferior vena cave 38. As shown in FIG. 13, the second medical device 326b may include an expandable member 328b. In some instances, the expandable member 328b may be referred to as an expandable medical balloon. The expandable member 328b may include a distal end and a proximal end. The proximal end of the expandable member 328b may be coupled to the elongate member 330b (described above).

Additionally, FIG. 13 illustrates that the medical device 310 may include one or more sensing members positioned adjacent to the first expandable member 328a and/or the second expandable member 328b. The sensing members illustrated in FIG. 13 may not extend through the inner lumens of the elongate member 330a or the elongate member 330b. For example, FIG. 13 illustrates the sensing members 332a and 334a positioned adjacent to the first expandable member 328a and the sensing members 332b and 334b positioned adjacent to the second expandable member 328b. The sensing members 332a, 334a, 332b and 334b may be similar in form and function as any of the sensing members described above. For example, the sensing members 332a, 334a, 332b and 334b may sense any of the physiological parameters described herein.

The materials that can be used for the various components of the system 10 (and/or other systems disclosed herein) may include those commonly associated with medical devices. However, this is not intended to limit the devices and methods described herein, as the discussion may be applied to other components, devices, or systems disclosed herein.

The components of the system 10 (and/or other systems disclosed herein) may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex® high-density polyethylene, Marlex® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys;

cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the components of the system 10 (and/or other systems disclosed herein) may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the components of the system 10 (and/or other systems disclosed herein) in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the components of the system 10 (and/or other systems disclosed herein) to achieve the same result.

In some embodiments, a degree of Magnetic Resonance Imaging (MRI) compatibility is imparted into the system 10 (and/or other systems disclosed herein). For example, components of the system 10 (and/or other systems disclosed herein), may be made of a material that does not substantially distort the image and create substantial artifacts (e.g., gaps in the image). Certain ferromagnetic materials, for example, may not be suitable because they may create artifacts in an MRI image. The components of the system 10 (and/or other systems disclosed herein) or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-NR and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A medical device system for treating a heart, the system comprising:
   a control system having a processor and a pump;
   a first elongate shaft having a proximal end coupled to the control system at a first location and a distal end, wherein a first expandable member is coupled to the first elongate shaft adjacent to the distal end of the first elongate shaft, wherein the first elongate shaft includes a first aperture positioned proximal to the first expandable member, and wherein the first expandable member is configured to be positioned in the superior vena cava after the first elongate shaft has been tracked through the jugular vein;
   a second elongate shaft having a proximal end coupled to the control system at a second location distinct from the first location and a distal end, wherein a second expandable member is coupled to the second elongate shaft adjacent to the distal end of the second elongate shaft, wherein the second elongate shaft includes a second aperture positioned proximal to the second expandable member, and wherein the second expandable member is configured to be positioned in the inferior vena cava after the second elongate shaft has been tracked through the femoral vein;
   a first sensing member extending within a portion of the first elongate shaft and through the first aperture, wherein the first sensing member includes a first end positioned proximal the first expandable member and a second end coupled to the control system, the first sensing member designed to sense a first parameter; and
   a second sensing member extending within a portion of the second elongate shaft and through the second aperture, wherein the second sensing member includes a first end positioned proximal the second expandable member and a second end coupled to the control system, the second sensing member designed to sense a second parameter; and
   a third sensing member having a first end configured to be positioned distal to the first expandable member, extending distally out of the distal end of the first elongate shaft, and adjacent the right atrium and a second end coupled to the control system, the third sensing member designed to sense a third parameter;
   wherein the processor is configured to assess a blood flow based on the first parameter, the second parameter or both the first parameter and the second parameter, and wherein the processor communicates with the pump to expand or contract the first expandable member, the second expandable member or both the first and the second expandable members based on a change in the blood flow.

2. The system of claim 1, wherein the third parameter is a blood pressure.

3. The system of claim 1, wherein the first sensing member, the second sensing member or both the first sensing member and the second sensing member includes a micro-electrical mechanical (MEMS) sensor.

4. The system of claim 1, wherein the first sensing member, the second sensing member or both the first sensing member and the second sensing member includes a fiber optic sensor.

5. The system of claim 1, wherein the first sensing member, the second sensing member or both the first sensing member and the second sensing member includes a fluid-filled pressure sensing catheter.

6. The system of claim 1, further comprising a fourth sensing member having a first end positioned adjacent the second expandable member and a second end coupled to the control system, the fourth sensing member designed to sense a fourth parameter.

7. The system of claim 6, wherein the first expandable member is positioned between a distal end of the first sensing member and a distal end of the third sensing member.

8. The system of claim 1, wherein the first elongate shaft has a plurality of lumens extending therein, and wherein at least a portion of the first sensing member extends within at least a portion of a first lumen of the plurality of lumens.

9. The system of claim 8, wherein at least a portion of the third sensing member extends within at least a portion of a second lumen of the plurality of lumens of the first elongate shaft.

10. The system of claim 1, further comprising a memory, the memory including a set of instructions executable by the processor, wherein the set of instructions is configured to expand both the first and the second expandable members based on a change in the first parameter, the second parameter or a change in both the first and the second parameters.

11. The medical system of claim 1, wherein the processor communicates with the pump to expand or contract the first expandable member, the second expandable member or both the first and the second expandable members to regulate blood flow in the superior vena cava, the inferior vena cava or both the superior vena cava and the inferior vena cava.

12. A medical device system for treating a heart, the system comprising:
a control system having a processor and a pump;
a first elongate shaft having a proximal end coupled to the control system and a distal end, wherein a first expandable member is coupled to the first elongate shaft adjacent to the distal end of the first elongate shaft, wherein the first elongate shaft includes a first aperture positioned proximal to the first expandable member, and wherein the first expandable member is configured to be positioned in the superior vena cava, and wherein all of the first elongate shaft is positioned proximal of the first expandable member when the first expandable member is positioned in the superior vena cava;
a second elongate shaft having a proximal end coupled to the control system and a distal end, wherein a second expandable member is coupled to the second elongate shaft adjacent to the distal end of the second elongate shaft, wherein the second elongate shaft includes a second aperture positioned proximal to the second expandable member, and wherein the second expandable member is configured to be positioned in the inferior vena cava, and wherein all of the second elongate shaft is positioned proximal of the second expandable member when the second expandable member is positioned in the inferior vena cava;
a first pressure sensing member extending through the first aperture and having a first end positioned proximal the first expandable member and a second end coupled to the control system, the first pressure sensing member designed to sense a first parameter;
a second pressure sensing member extending through the second aperture and having a first end positioned proximal the second expandable member and a second end coupled to the control system, the second pressure sensing member designed to sense a second parameter;
a third pressure sensing member having a first end configured to be positioned distal to the first expandable member, wherein the third pressure sensing member extends distally out of the distal end of the first elongate shaft, and adjacent the right atrium and, wherein the third pressure sensing member includes a second end coupled to the control system, the third pressure sensing member designed to sense a third parameter; and
a fourth pressure sensing member having a first end positioned distal the second expandable member and a second end coupled to the control system, the fourth pressure sensing member designed to sense a fourth parameter;
wherein the processor is configured to assess a blood flow based on the first parameter, the second parameter or both the first parameter and the second parameter, and wherein the processor communicates with the pump to expand or contract the first expandable member, the second expandable member or both the first and the second expandable members based on a change in the blood flow.

13. The system of claim 12, wherein the wherein the first parameter, the second parameter or both the first parameter and the second parameter is blood pressure.

14. The system of claim 12, wherein the first pressure sensing member, the second pressure sensing member or both the first pressure sensing member and the second pressure sensing member includes a MEMS sensor.

15. The system of claim 12, wherein the first pressure sensing member, the second pressure sensing member or both the first pressure sensing member and the second pressure sensing member includes a fiber optic sensor.

16. The system of claim 12, wherein the first expandable member is positioned between a distal end of the first pressure sensing member and a distal end of the third pressure sensing member.

17. The system of claim 12, further comprising a memory, the memory including a set of instructions executable by the processor, wherein the set of instructions is configured to expand both the first and the second expandable members based on a change in the first parameter, the second parameter or a change in both the first and the second parameters.

18. A method for treating the heart, the method comprising:
advancing a first medical device into the superior vena cava through the jugular vein, the first medical device including a first elongate shaft having a first aperture and a proximal end coupled to a control system and a distal end, wherein a first expandable member is coupled to the first elongate shaft adjacent to the distal end of the first elongate shaft, and wherein the first medical device further includes a first sensing member extending through the first aperture and coupled to the control system;
advancing a second medical device into the inferior vena cava through the femoral vein, the second medical device including a second elongate shaft having a second aperture and a proximal end coupled to a control system and a distal end, wherein a second expandable member is coupled to the second elongate shaft adjacent to the distal end of the second elongate shaft, and wherein the second medical device further include a second sensing member extending through the second aperture and coupled to the control system;
advancing a third sensing member within the first elongate shaft to a position adjacent the right atrium, wherein the third sensing member extends distally out of the distal end of the first elongate shaft;
sensing a first parameter with the first sensing member;
sensing a second parameter with the second sensing member;
sensing a third parameter with the third sensing member;
analyzing a blood flow based on the first parameter, the second parameter or both the first and the second parameter; and
expanding the first expandable member, the second expandable member or both the first and the second expandable members based on a change in the blood flow.

* * * * *